(12) United States Patent
Tornier et al.

(10) Patent No.: US 8,821,503 B2
(45) Date of Patent: Sep. 2, 2014

(54) ANCILLARY TOOL AND METHOD FOR POSITIONING A PROSTHETIC ACETABULUM OF A HIP PROSTHESIS

(75) Inventors: Alain Tornier, St. Ismier (FR);
Jean-Pierre Berger, Beaufays (BE);
Patrick Reynaud, Lyons (FR); Arnaud Godeneche, Dommartin (FR);
Christophe Hulet, Caen (FR);
Jean-Claude Panisset, Le Versoud (FR);
Philippe Deroche, Dracy le Fort (FR);
Jean Puget, Toulouse (FR); Andre Ferreira, Caluire (FR)

(73) Assignee: Tornier SAS, Montbonnot Saint Martin (FR)

( * ) Notice: Subject to any disclaimer, the term of this patent is extended or adjusted under 35 U.S.C. 154(b) by 1438 days.

(21) Appl. No.: 12/145,301

(22) Filed: Jun. 24, 2008

(65) Prior Publication Data
US 2008/0255568 A1 Oct. 16, 2008

Related U.S. Application Data

(62) Division of application No. 10/758,280, filed on Jan. 16, 2004, now Pat. No. 7,396,357.

(30) Foreign Application Priority Data

Jan. 17, 2003 (FR) ...................................... 03 00524

(51) Int. Cl.
*A61B 17/56* (2006.01)
(52) U.S. Cl.
USPC ............................................................ 606/91
(58) Field of Classification Search
USPC ................................................ 606/81, 91, 99
See application file for complete search history.

(56) References Cited

U.S. PATENT DOCUMENTS

| 3,859,992 A | 1/1975 | Amstutz |
| 4,305,394 A | 12/1981 | Bertuch, Jr. |

(Continued)

FOREIGN PATENT DOCUMENTS

| DE | 4215888 | 11/1993 |
| DE | 10031271 | 1/2002 |

(Continued)

OTHER PUBLICATIONS

Search Report from European application No. EP 04356004, dated Mar. 31, 2004, 2 pp.

(Continued)

*Primary Examiner* — Mary Hoffman
(74) *Attorney, Agent, or Firm* — Knobbe Martens Olson & Bear, LLP

(57) ABSTRACT

The ancillary tool according to the invention comprises a handle for manipulating an acetabulum provided, in its distal part, with a head for gripping the acetabulum and, in its proximal part, with a surface for application of a force of impaction. The tool further comprises at least one added endpiece adapted to be removably connected to the distal end of the handle. This endpiece defines both a face for wedging the acetabulum and an opposite face for interaction of the endpiece with the head of the handle, these faces both being borne by a radially deformable supple ring. The invention is particularly applicable to the positioning of an acetabular prosthesis in an anatomical or prosthetic cavity of a patient's hip.

31 Claims, 4 Drawing Sheets

(56) References Cited

U.S. PATENT DOCUMENTS

| | | |
|---|---|---|
| 4,632,111 A | 12/1986 | Roche |
| 4,716,894 A | 1/1988 | Lazzeri et al. |
| 5,098,437 A | 3/1992 | Kashuba et al. |
| 5,116,339 A | 5/1992 | Glock |
| 5,169,399 A | 12/1992 | Ryland et al. |
| 5,171,289 A | 12/1992 | Tornier |
| 5,314,485 A | 5/1994 | Judet |
| 5,326,359 A | 7/1994 | Oudard |
| 5,358,526 A | 10/1994 | Tornier |
| 5,364,403 A | 11/1994 | Peterson et al. |
| 5,405,399 A | 4/1995 | Tornier |
| 5,417,696 A | 5/1995 | Kashuba et al. |
| 5,429,639 A | 7/1995 | Judet |
| 5,458,650 A | 10/1995 | Carret et al. |
| 5,505,731 A | 4/1996 | Tornier |
| 5,540,697 A | 7/1996 | Rehmann et al. |
| 5,571,111 A | 11/1996 | Aboczky |
| 5,571,200 A | 11/1996 | Cohen et al. |
| 5,584,837 A | 12/1996 | Peterson |
| 5,591,168 A | 1/1997 | Judet et al. |
| 5,619,399 A | 4/1997 | Mok |
| 5,662,651 A | 9/1997 | Tornier et al. |
| 5,676,702 A | 10/1997 | Ratron |
| 5,683,399 A | 11/1997 | Jones |
| 5,702,447 A | 12/1997 | Walch et al. |
| 5,702,457 A | 12/1997 | Walch et al. |
| 5,702,478 A | 12/1997 | Tornier |
| 5,766,256 A | 6/1998 | Oudard et al. |
| 5,824,106 A | 10/1998 | Fournol |
| 5,879,395 A | 3/1999 | Tornier et al. |
| 5,976,148 A | 11/1999 | Charpenet et al. |
| 6,022,357 A | 2/2000 | Reu et al. |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,206,925 B1 | 3/2001 | Tornier |
| 6,299,646 B1 | 10/2001 | Chambat et al. |
| 6,328,758 B1 | 12/2001 | Tornier et al. |
| 6,334,874 B1 | 1/2002 | Tornier et al. |
| 6,379,387 B1 | 4/2002 | Tornier |
| 6,454,809 B1 | 9/2002 | Tornier |
| 6,488,712 B1 | 12/2002 | Tornier et al. |
| 6,540,770 B1 | 4/2003 | Tornier et al. |
| 6,582,469 B1 | 6/2003 | Tornier |
| 6,599,295 B1 | 7/2003 | Tornier et al. |
| 6,626,946 B1 | 9/2003 | Walch et al. |
| 6,743,235 B2 * | 6/2004 | Subba Rao .................. 606/91 |
| 6,761,740 B2 | 7/2004 | Tornier |
| 6,767,368 B2 | 7/2004 | Tornier |
| 6,802,864 B2 | 10/2004 | Tornier |
| 6,824,567 B2 | 11/2004 | Tornier et al. |
| 6,890,357 B2 | 5/2005 | Tornier |
| 6,969,406 B2 | 11/2005 | Tornier |
| 7,033,396 B2 | 4/2006 | Tornier |
| 2002/0169455 A1 | 11/2002 | Bannerman et al. |
| 2003/0009170 A1 | 1/2003 | Tornier |
| 2003/0009171 A1 | 1/2003 | Tornier |
| 2003/0028198 A1 | 2/2003 | Tornier et al. |
| 2004/0134821 A1 | 7/2004 | Tornier |
| 2004/0210220 A1 | 10/2004 | Tornier |
| 2004/0230197 A1 | 11/2004 | Tornier et al. |
| 2005/0049709 A1 | 3/2005 | Tornier |
| 2005/0055102 A1 | 3/2005 | Tornier et al. |
| 2005/0071015 A1 | 3/2005 | Sekel |
| 2005/0165490 A1 | 7/2005 | Tornier |
| 2005/0203536 A1 | 9/2005 | Laffargue et al. |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288791 A1 | 12/2005 | Tornier et al. |
| 2006/0015185 A1 | 1/2006 | Chambat et al. |
| 2006/0173457 A1 | 8/2006 | Tornier |
| 2006/0235538 A1 | 10/2006 | Rochetin |
| 2007/0043265 A1 | 2/2007 | Rochetin |
| 2007/0173947 A1 | 7/2007 | Ratron et al. |
| 2007/0179628 A1 | 8/2007 | Rochetin |
| 2007/0270718 A1 | 11/2007 | Rochetin et al. |

FOREIGN PATENT DOCUMENTS

| | | |
|---|---|---|
| FR | 2797180 | 2/2001 |
| GB | 2299758 | 10/1996 |
| WO | WO 94/21199 | 9/1994 |
| WO | WO 95/11641 | 5/1995 |
| WO | WO 02/074203 | 9/2002 |

OTHER PUBLICATIONS

Search Report from French application No. FR 0300524, dated Oct. 21, 2003, 2 pp.

* cited by examiner

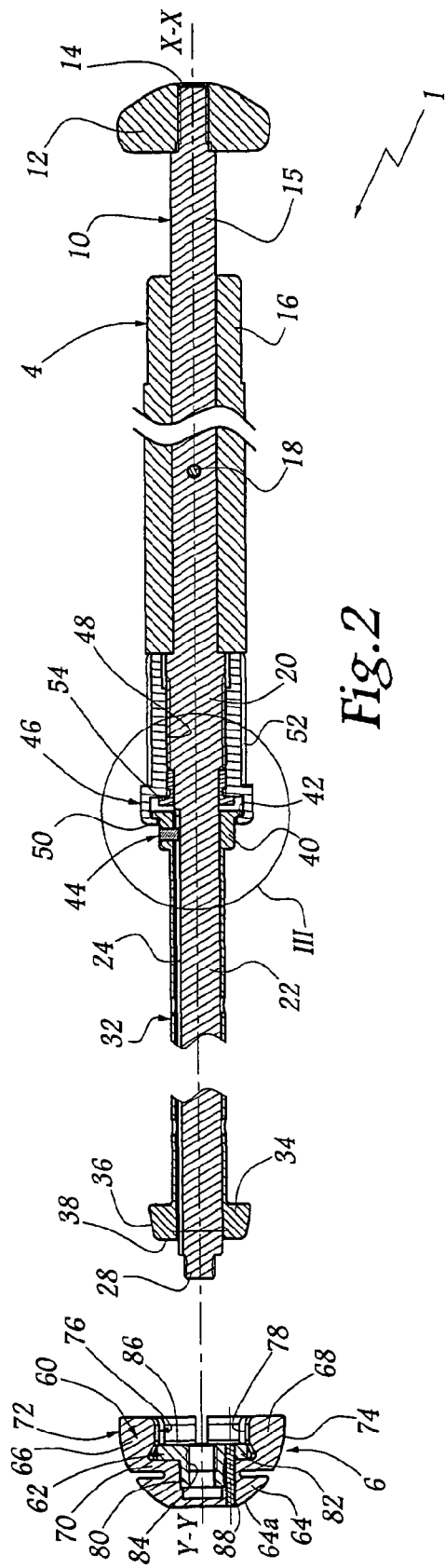

ANCILLARY TOOL AND METHOD FOR POSITIONING A PROSTHETIC ACETABULUM OF A HIP PROSTHESIS

REFERENCE TO RELATED APPLICATIONS

This application is a divisional of U.S. application Ser. No. 10/758,280, filed Jan. 16, 2004, now U.S. Pat. No. 7,396,357, and entitled ANCILLARY TOOL AND METHOD FOR POSITIONING A PROSTHETIC ACETABULUM OF A HIP PROSTHESIS, which claims priority to France Patent Application 03 00524 filed Jan. 17, 2003, both are hereby incorporated by reference.

FIELD OF THE INVENTION

The present invention relates to an ancillary tool for positioning an acetabular prosthesis in an anatomical or prosthetic cavity of a patient's hip, of the type comprising a handle for manipulating the acetabulum provided, in its distal part, with a head for gripping the acetabulum and, in its proximal part, with a surface for application of a force of impaction.

BACKGROUND OF THE INVENTION

This type of ancillary tool, commonly called "gripper/impactor tool", is used during surgical operations for implanting a rigid acetabulum, generally made of metal, in the patient's hip. Once the acetabulum has been implanted in the bone, a polymer cup is housed in the acetabulum, this cup being itself intended to receive the hemispherical head of a femoral implant or of the anatomical femur. The polymer cup is either connected directly to the acetabulum, by wedging of corresponding truncated surfaces borne by the cup and the acetabulum, or connected to a metallic shell which is received in articulated manner, substantially in the manner of a ball-and-socket joint, in the acetabulum fixed to the bone. A cotyloidal assembly with double mobility is spoken of in the latter case.

A first example of this type of ancillary tool consists in a rigid handle at the distal end of which is permanently connected a head made of supple plastics material, such as Ertafluor (Registered Trademark). This head, whose outer dimensions are slightly greater than the inner dimensions of the acetabulum to be implanted, is introduced and wedged in this acetabulum, allowing gripping then positioning thereof up to the location of impaction of the hip. However, the use of such a one-piece head presents numerous drawbacks, as the supple material used does not allow an efficient grip if the inner dimensions of the acetabulum are not adapted to those of the head, this often obliging the surgeon to seize the acetabulum to be implanted in one hand, in order to wedge the head efficiently. The conditions of sterility are therefore not always respected. Moreover, the supple material of the head is often difficult to sterilize. Furthermore, once the impaction of the acetabulum is effected, it is generally difficult to disengage the head wedged in the acetabulum.

U.S. Pat. No. 5,169,399 discloses another example of such a tool in which a gripper/impactor handle is adapted for positioning a prosthetic assembly constituted by a metallic acetabulum and a polymeric insert, the acetabulum and the insert being positioned and impacted simultaneously by the handle. The latter presents at its distal end a split head whose two jaws are spaced apart from each other by a compression spring. When the surgeon brings the two jaws towards each other by compressing the spring, the head may be introduced inside the polymeric insert, then, by releasing one of the jaws, the prosthetic assembly formed by the insert and the acetabulum retained on the insert undergoes a gripping effort by the head. This tool is complex to make and to manipulate, the effort of grip depending directly on the force of the compression spring interposed between the jaws of the head. Moreover, insofar as the zone of contact between the head of the tool and the prosthetic assembly is formed by the end part of the polymeric insert of greatest diameter, the effort of impaction applied by the handle on the prosthetic assembly cannot attain high values without risk of damage to the insert and the guiding of the acetabulum by the head during impaction is unreliable. Under these conditions, there is no guarantee that the surgeon will not use one of his hands to hold the prosthetic assembly during grip thereof by the tool. Furthermore, this tool is not applicable to the positioning of a cotyloidal assembly with double mobility set forth hereinabove, the grip of the insert not ensuring hold of the acetabulum to be implanted.

Document WO 95/11641 discloses another tool of the afore-mentioned type, which further comprises a metallic endpiece removably added to the distal end of the handle for manipulating the acetabulum to be implanted. A deformable member of the endpiece is constituted by four quadrants, namely two diametrically opposite rigid quadrants fixedly connected to a proximal part of the endpiece by bridges of matter, and two diametrically opposite mobile quadrants, each connected to one of the rigid quadrants by an elastically deformable hinge. Pivoting of the two mobile quadrants is controlled by screwing the handle in the proximal part of the endpiece. However, the use of these two mobile quadrants ensures an efficient wedging of the acetabulum only in two diametrically opposite zones of its inner face, in other words only with a limited gripping force.

It is an object of the present invention to propose a tool which is adapted to acetabula of different dimensions and nature and which ensures both an efficient grip of the acetabulum and a good application of the force of impaction, without hindering the withdrawal of the tool once positioning has been effected.

SUMMARY OF THE INVENTION

To that end, the invention relates to an ancillary tool for positioning an acetabular prosthesis in an anatomical or prosthetic cavity of a patient's hip comprising a handle for manipulating the acetabulum provided, in its distal part, with a head for gripping the acetabulum and, in its proximal part, with a surface for application of a force of impaction, and at least one added endpiece adapted to be removably connected to the distal end of the handle and defining both a face for wedging the acetabulum and an opposite face for interaction of the endpiece with the head of the handle, wherein the endpiece comprises a supple ring radially deformable with respect to the longitudinal axis of the endpiece, on which are formed the wedging and interaction faces.

The use of the radially deformable ring makes it possible both to guarantee an efficient grip, the surgeon being able to control hold of the endpiece by the head of the handle, and to efficiently transmit at least a part of the effort of impaction up to the acetabulum. By having available a series of endpieces of different sizes, the surgeon is able to use the same manipulation handle for positioning acetabula of different dimensions and/or nature.

According to other characteristics of this ancillary tool, taken separately or in all technically possible combinations:

the ring is radially deformable over substantially the whole of its periphery;

the face of the endpiece intended for wedging the acetabulum is constituted by substantially the whole outer face of the ring;

the endpiece comprises both a supple part including the deformable ring and a rigid part fast with the supple part and provided with means for removable connection to the distal end of the handle;

the rigid part of the endpiece is constituted by a metallic insert fixed to the supple part;

the deformable ring is elastically connected to a base of the supple part;

the deformable ring comprises a plurality of petals, the wedging and interaction faces being respectively constituted by the outer and inner surfaces of each of these petals;

the rigid part of the endpiece defines a stop surface, in the longitudinal direction of the handle, for the head of the handle;

the supple part of the endpiece presents at least one surface for transmission of the force of impaction between the handle and the acetabulum;

the head of the handle defines a ramp surface adapted to cooperate with the interaction face of the endpiece;

the handle comprises a rigid rod on which the head is movably mounted, as well as means for driving the head with respect to the rod in a movement of translation in the longitudinal direction of the rod;

the handle comprises a sleeve disposed coaxially to the rod and at the distal end of which the head is rigidly fixed and the means for driving the head with respect to the rod comprise a grip screwed on the rod and connected in translation with the sleeve, this sleeve being immobilized in rotation with respect to the rod; and a ring is axially interposed between the sleeve and the screwed grip.

The invention also relates to a method for positioning an acetabular prosthesis in an anatomical or prosthetic cavity of a patient's hip, comprising the steps of:

using, on the one hand, a handle for manipulating the acetabulum, provided, in its distal part, with a head for gripping the acetabulum and, at its proximal end, with a surface for application of a force of impaction, and, on the other hand, a series of endpieces of different dimensions and/or geometry, each comprising a supple ring radially deformable with respect to the longitudinal axis of the endpiece, on which are formed both a face for wedging the acetabulum and an opposite face for interaction of the endpiece with the head of the handle;

selecting, from the series of endpieces, an endpiece of which the wedging face is substantially complementary of the inner wall of the acetabulum to be positioned;

connecting the endpiece to the distal end of the handle;

placing the endpiece in the acetabulum;

placing the endpiece in engagement by the head of the handle so as to provoke radial deformation of the ring and consequently grip of the acetabulum by the endpiece;

positioning the acetabulum in the cavity of the patient's hip;

applying a force of impaction on the corresponding surface of the handle;

disengaging the head from the endpiece; and withdrawing the endpiece from the positioned acetabulum.

BRIEF DESCRIPTION OF THE DRAWINGS

The invention will be more readily understood on reading the following description given solely by way of example and with reference to the accompanying drawings, in which:

FIG. 2 is a longitudinal section through the tool of FIG. 1.

FIG. 3 is a view of detail III in FIG. 2.

DESCRIPTION OF PREFERRED EMBODIMENT

Figure 1:
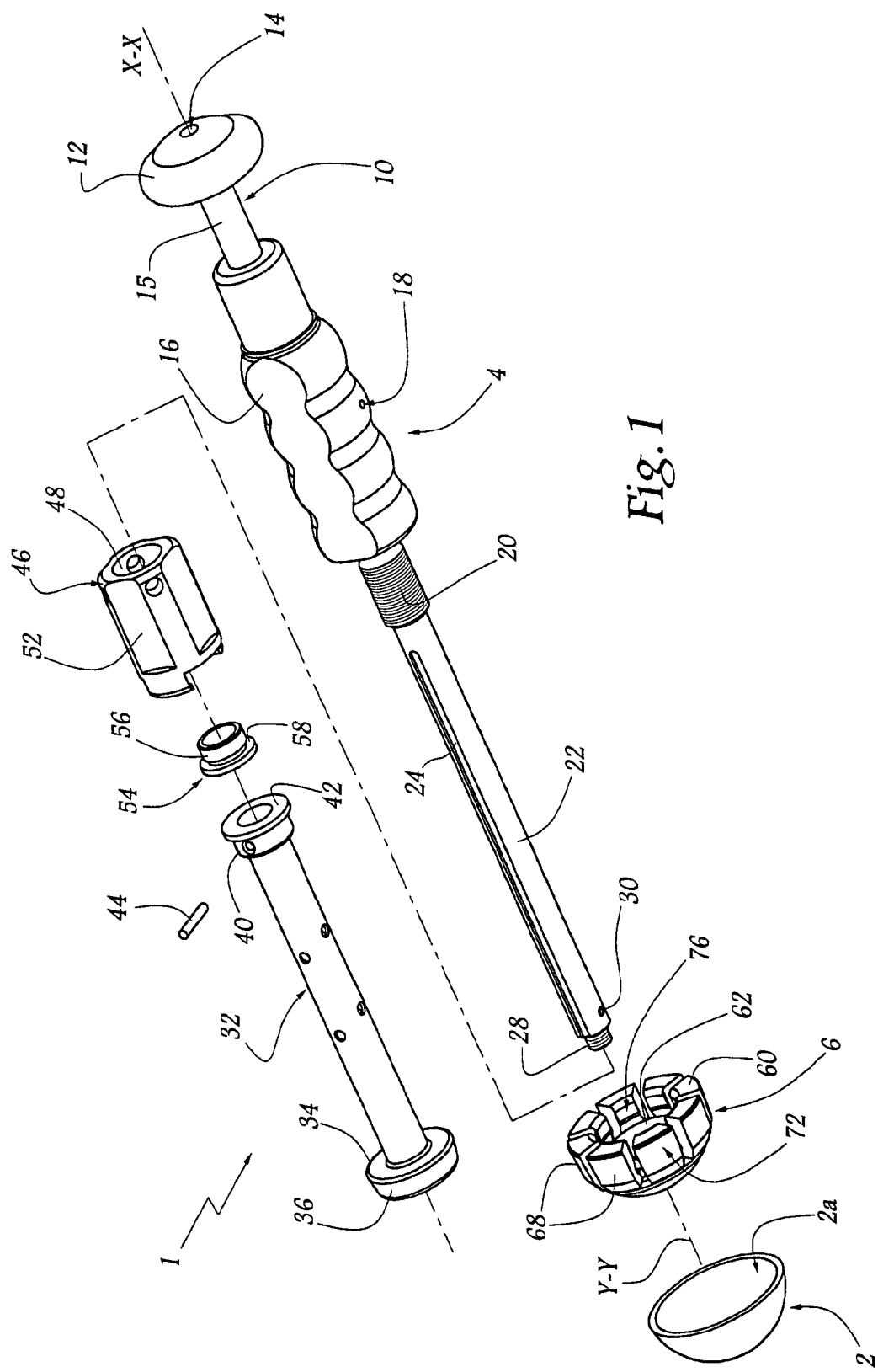
FIG. 1 is an exploded view in perspective of an ancillary tool according to the invention, and of an acetabular prosthesis.

Referring now to the drawings, and firstly to FIGS. 1 to 3, an ancillary tool 1 for positioning a metallic acetabular prosthesis 2 is shown. This tool essentially comprises a handle 4 extending about an axis X-X and an added endpiece 6 adapted to be removably connected to the distal end of the handle. The acetabulum 2 comprises a substantially hemispherical inner wall 2a and is intended to form, with an internal shell (not shown), a cotyloidal assembly with double mobility as set forth hereinbefore.

The handle 4 comprises a rigid rod 10 at the proximal end of which is rigidly fixed a knob 12. This knob presents a slightly convex proximal surface 14, forming a surface for application of a force of impaction.

Passing from the proximal end of the rod 10 towards its distal end, the rod comprises a first cylindrical section 15 on which is fixedly added a knob 16 for manipulation, connected to the rod by, for example, a tapered pin 18. The rod then comprises a threaded section 20 of diameter larger than the section 15, then a smooth section 22 of smaller diameter and on the outer surface of which is formed a longitudinal groove 24. The distal end of the rod is formed by a projecting catch 28 coaxial to the axis X-X and threaded.

The handle 4 also comprises a tubular sleeve 32 mobile with respect to the rod 10 and arranged coaxially to sections 20 and 22. This sleeve is provided at its distal end with a head 34 whose outer shape is truncated and convergent towards the distal end of the handle. Consequently this head defines a truncated ramp surface 36 as well as a substantially planar distal surface 38.

The proximal end of the sleeve 32 forms a substantially cylindrical foot 40 from which a projecting end flange 42 extends radially.

The foot 40 is provided with a cylindrical pin 44 which extends inside a substantially complementary recess formed in a direction radial with respect to axis X-X. The length of this pin is greater than the thickness of the foot, with the result that a part of the pin extends inside the sleeve 32 and is engaged in the longitudinal groove 24 of the rod 10. The sleeve 32 is thus immobilized in rotation with respect to the rod, but free to move in a movement of translation in the direction X-X.

The ancillary tool 1 comprises means for driving the sleeve 32 in translation with respect to the rod 10, these means being in the form of a tubular body 46 of generally cylindrical shape and essentially disposed coaxially with respect to the threaded section 20. Internally, the body 46 defines a tapping 48 complementary of the section 20 of the rod 10. At its distal end, the body 46 is provided with two diametrically opposite re-entrant flanges 50 spaced apart from each other by a distance greater than the outer diameter of the end flange 42 of the sleeve 32. Consequently, these flanges 50 form for the sleeve 32 hooks for drive in direction X-X. Externally, the body 46 presents flat portions 52 ensuring correct grip of the body with a view to urging it in a movement of rotation about its axis.

A ring 54, made of synthetic material, for example polyacetal, is axially interposed between the sleeve 32 and the tubular body 46. More precisely, this ring comprises a cylindrical body 56 presenting an outer thread complementary of the thread of the tapping 48, and an annular skirt 58 of outer diameter greater than the diameter of the recess 48. The skirt 58 forms a protective layer for the sleeve 32 when the rod 10, and therefore the body 46 screwed on this rod, is under stress, by application of a force of impaction on the knob 12.

As for the endpiece 6, it extends about an axis Y-Y, coaxial to axis X-X in FIG. 2. It is formed by a supple body 60, constituted for example by polyacetal, and by a metallic insert 62 connected to the body 60 by, for example, a pin 88.

More precisely, the body 60 comprises a hemispherical base 64 whose outer shape is substantially complementary of the inner wall 2a of the acetabulum 2, as well as a ring 66 of petals 68 connected to the base 64 by elastically deformable connecting zones 70. By simultaneous deformation of these zones 70, the ring 66 presents a considerable capacity of radial deformation with respect to axis Y-Y. In other words, the ring 66 is radially deformable over substantially the whole of its periphery, the petals 68 being able to move apart radially in homogeneous manner.

To that end, the ring 66 defines a face 72 for wedging the acetabulum 2, constituted by the outer surfaces 74 substantially in the form of spherical frustum of each of the petals 68, and a face 76 for interaction of the endpiece 6 with the head 34 of the sleeve 32, constituted by the inner surfaces 78 of the petals 68 which form counter-ramp surfaces for the ramp surface 36 of the head 34. Each inner surface 78 comprises a cylindrical part extended rearwardly by a flared part convergent towards the base 64.

The metallic insert 62 is formed by a cylinder 80 from which a flange 82 extends radially at one of its ends. The cylinder 80 is screwed in the base 64 of the body 60 and forms a tapping 84 complementary of the projecting catch 28 fast with the rod 10. The flange 82 forms a stop surface 86 for the planar surface 38 of the head 34.

The ancillary tool 1 is used as follows.

Considering the handle 4 in the mounted state as shown in FIG. 2, the surgeon introduces the distal end of the rod 10 in the endpiece 6, rendering axes X-X and Y-Y coaxial. The endpiece 6 is connected to the handle 4 by screwing the catch 28 in the tapping 84 of the insert 62. The surgeon then grips the tool in one hand at the level of the manipulation knob 16 and in the other hand at the level of the body 46 forming grip, and rotates the grip 46 with respect to the rod 10 in clockwise direction, observing the body from its proximal end. In the manner of a screw-nut system, the grip 46 pushes the sleeve 32 in a movement of translation along axis X-X, taking the head 34 inside the ring 66 of the endpiece. By continuing this drive movement, the ramp surface 36 cooperates with the counter-ramp surfaces 78 borne internally by the petals 68 so as to radially expand the ring 66 and thus apply the outer surfaces 74 of the petals against the inner wall of the acetabulum 2. In other words, the ring 66 passes from a configuration of rest to an outwardly expanded configuration, of which the substantially circular outer contour presents a diameter greater than that of the contour of the ring in its configuration of rest. It will be understood that the whole outer face 74 of the ring 66 then participates in the wedging of the acetabulum 2. In this respect it will be noted that, for the tool 1 shown, the petals 68 of this ring are identical, which does not limit the invention in that the radial deformation of the ring by the head of the tool must be provided in particular to bring about the virtually simultaneous abutment of the essential of the outer surface of the ring on the inner concave face of the acetabulum to be manipulated.

The surgeon continues this movement until he considers that the endpiece is sufficiently retained by the head to guarantee a correct grip of the acetabulum by the endpiece by wedging. The stop surface 86 borne by the endpiece avoids any risk of excessive deformation of the petals, the insert 62 thus imposing a maximum axial position for the head 34.

The surgeon then manipulates the acetabulum freely with the aid of the ancillary tool 1, positions it on the patient's hip at the level of an anatomical cavity or a prosthetic one, i.e. formed by a previously implanted bone-reconstructing plate. Then, with the aid of a suitable hammer, he applies a force of impaction on the surface 14. The effort of impaction is transmitted in the direction X-X of rod 10 to the rigid insert 62 which is screwed on this rod, then from the insert to the base 64 of the supple body 62, and finally from this base to the acetabulum 2 through the outer surface 64a of the base, causing the acetabulum to be force-fitted in the corresponding cavity of the hip.

Once the impaction is effected, the surgeon rotates the grip 46 with respect to the rod 10 in anti-clockwise direction so as to disengage the head 34 from the endpiece 6. By elastic return deformation of the connecting zones 70, the petals 68 resume their initial position, making it possible to withdraw the endpiece from the implanted acetabulum without effort.

The ancillary tool according to the invention thus makes it possible easily to manipulate an acetabular prosthesis to be implanted, and with precision. The surgeon is at no moment obliged to touch the acetabulum with his hands. The effort of impaction is efficiently transmitted to the acetabulum, in the longitudinal direction of the handle 4, and this through the supple part of the endpiece. The risks of marking, and even damaging the impacted acetabulum are thus limited, unlike the impactor tools disclosed in the prior art, such as those envisaged in U.S. Pat. No. 5,169,399 and WO-95/11641 mentioned hereinbefore, for which hard parts of the tools are applied directly on the edge of the acetabulum, in other words at the level of a fragile zone of restricted area.

Figure 4:
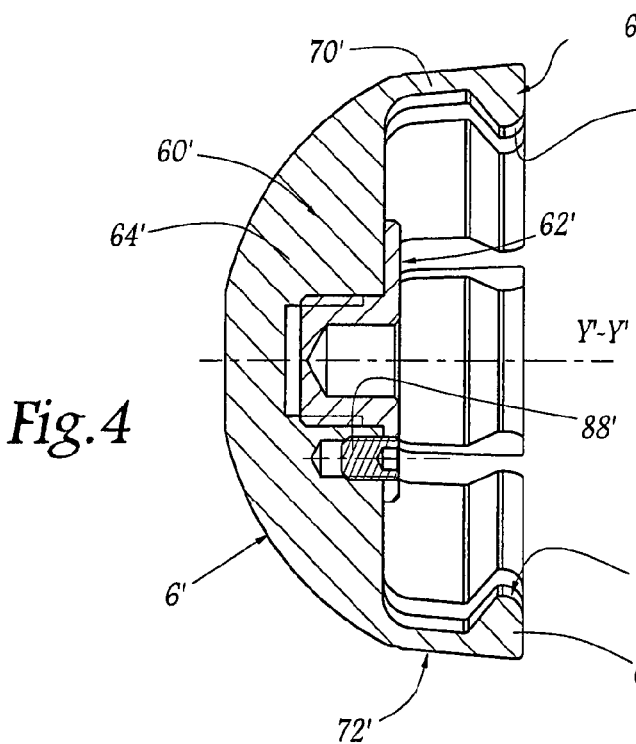
FIG. 4 is a longitudinal section of a variant endpiece of the tool of FIG. 1.

The ancillary tool according to the invention advantageously comprises a series of endpieces whose dimensions and geometries are different. For example, this series comprises, in addition to endpiece 6, an endpiece 6' shown in FIG. 4, having the same general structure as the endpiece 6, but of which the outer face of the supple body is formed for an acetabulum whose inner wall is partly truncated. This endpiece is adapted for the grip and impaction of acetabula in which a polymeric insert is directly connected by wedging.

More precisely, the endpiece 6' is essentially constituted by the same elements as the endpiece 6, these latter having the same reference figures to which a prime is added. In this way, endpiece 6' comprises a body 60' of supple material and a rigid insert 62', rigidly fixed to each other by a screw 88'. Apart from the geometry of its outer face, endpiece 6' of axis Y'-Y' differs essentially from endpiece 6 by the shape of its petals 68' and the zones 70' for connection with the base 64'; the outer face 74' of each petal 68' is truncated, convergent towards the base, the inner face 78' of each petal is flared over the whole of its length and the connection zones 70' extend parallel to axis Y'-Y'.

Figure 5:
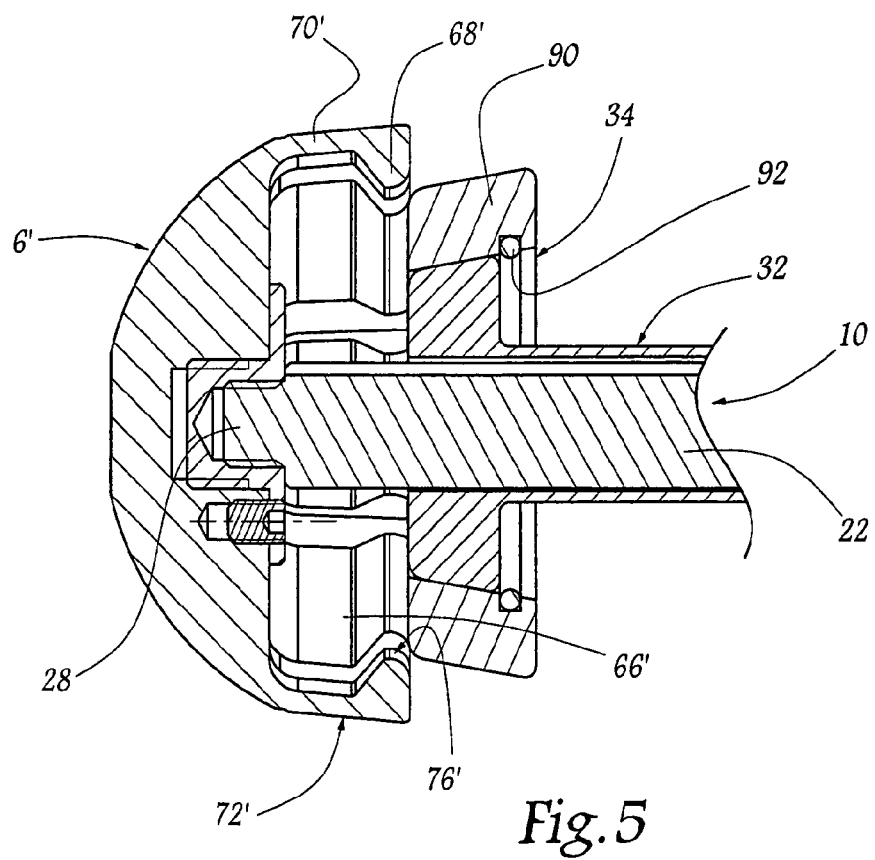
FIG. 5 is a longitudinal section of a part of the tool provided with the endpiece of FIG. 4.

As shown in FIG. 5, the head 34 of the handle 4 is then equipped with a bush 90 connected to the rest of the sleeve 32 by a retaining clip 92. This bush increases the outer dimension of the head 34 so as to adapt the latter to the endpiece 6' and thus laterally defines a ramp surface adapted to cooperate with the interaction face 76' of the endpiece.

The use of the ancillary tool 1 provided with the endpiece 6' is substantially similar to the use described previously. During the application of the effort of impaction, the force is essentially transmitted to the acetabulum by the truncated surfaces 74' of the petals 68'.

Figure 6:
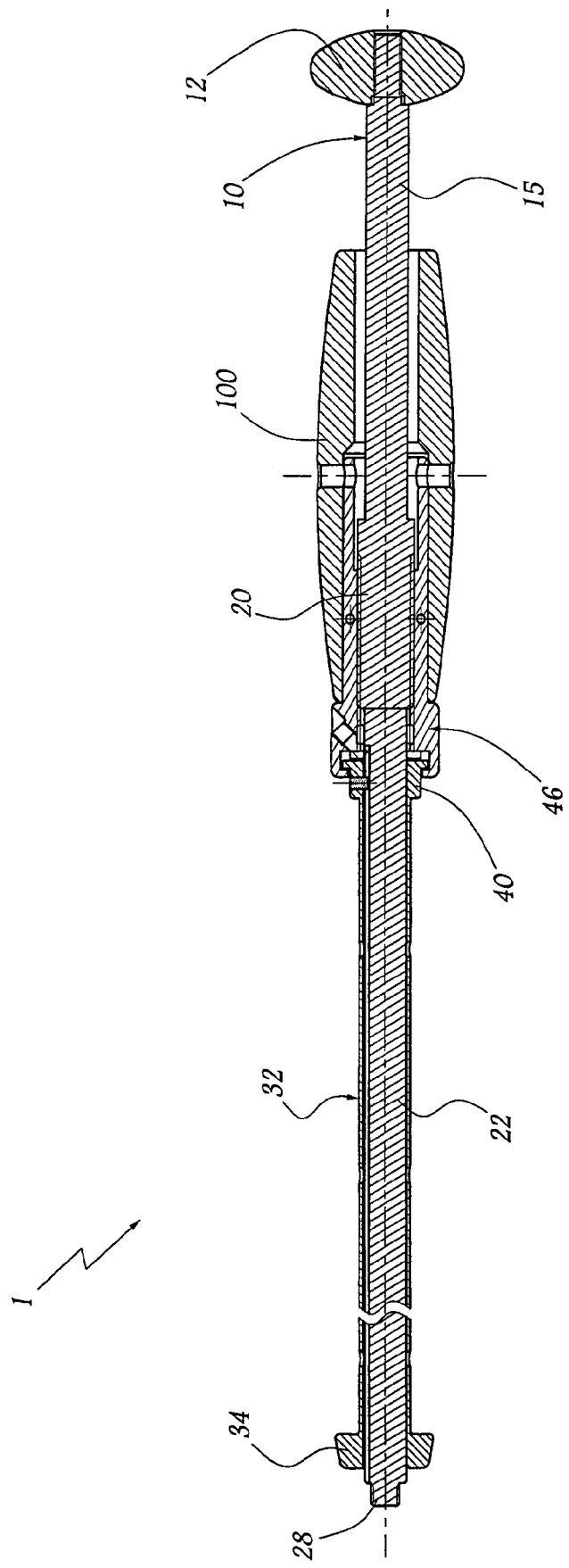
FIG. 6 is a longitudinal section through a variant of a tool according to the invention.

FIG. 6 shows a variant of the ancillary tool 1 which essentially differs from the tool of FIGS. 1 to 3 by the following:

Contrarily to the manipulation handle 16 of the preceding Figures, which is rigidly connected to the rod 10, the ancillary tool of FIG. 6 comprises a manipulation handle 100 which is connected to the grip 46 screwed on the rod 10. The use of this variant is substantially similar to that of the tool of FIGS. 1 to 3, the user having, in order to provoke the displacement of the head 34 in translation with respect to the rod 10, to apply a movement of rotation on the grip 46/handle 100 assembly, for example by gripping the handle 100 in one hand and the knob 12 with the other hand.

Various arrangements and variants of the ancillary tool according to the invention may also be envisaged:

materials other than polyacetal may be used for making the supple body of the endpiece 6, the materials retained having both to combine a good shock resistance by reason of the transmission of the efforts of impaction, and a good resistance to sterilization, and not to damage the inner wall of the acetabulum to be implanted; and/or the endpiece added to the distal end of the handle of the ancillary tool is formed in one piece, for example of synthetic material, formed by a supple part comprising a ring which is radially deformable in homogeneous manner, similar to ring 66, and by a more rigid part, for example of reinforced material, in which the handle is removably connectable.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. An ancillary tool for positioning and seating a prosthetic acetabulum in an anatomical or prosthetic cavity of a patient's hip, the tool comprising an endpiece and a handle adapted to manipulate the acetabulum, the endpiece comprising an elastically deformable ring including a plurality of petals, the handle including a rod and a head, the tool having a first configuration in which the head is coupled with the rod and disengaged from the elastically deformable ring permitting the petals to elastically contract with respect to a longitudinal axis of said endpiece and a second configuration in which the head is coupled with the rod and is received in the elastically deformable ring, the petals of the elastically deformable ring including outer surfaces adapted to wedge against the inner surface of the acetabulum and opposite inner surfaces adapted to interact said endpiece with said handle when the tool is in the second configuration, wherein said endpiece includes a supple part and a rigid part secured to the supple part, wherein the rigid part includes structure for removably securing the rod to the endpiece and wherein said handle further includes elements for applying a first force to urge said head into cooperative engagement with said inner surfaces of said petals of the elastically deformable ring in the second configuration to thereby radially expand said petals of the elastically deformable ring with respect to the longitudinal axis of said endpiece, wherein said elements include a threaded portion on the rod, a grip screwed on the threaded portion and a movable sleeve fitted between the grip and the head.

2. The ancillary tool of claim 1, wherein the grip is adapted to longitudinally move the sleeve with respect to the rod to engage the endpiece and wherein the sleeve is adapted to impart the first force when the grip is rotated to move the sleeve into engagement with the endpiece.

3. The ancillary tool of claim 1, wherein the rigid part of the endpiece includes a tapped section adapted to be secured to a threaded section on a distal end of the rod.

4. The ancillary tool of claim 3, wherein the endpiece is secured to the rod by screwing the threaded section on the distal end of the rod into the tapped section of the rigid part of the endpiece.

5. The ancillary tool of claim 1, wherein the tool includes a knob fixed to a proximal end of the tool.

6. The ancillary tool of claim 5, wherein the tool is adapted to transmit an impact force imparted on the knob to the proximal end of the tool.

7. The ancillary tool of claim 1, wherein the elastically deformable ring is elastic such that the ring expands from the first configuration to the second configuration with the application of the first force and contracts substantially to the first configuration when the first force is removed.

8. The ancillary tool of claim 1, wherein the petals are adapted to move apart radially in a homogenous manner when contacted by the head.

9. The ancillary tool of claim 1, wherein the outer surfaces of the petals of the elastically deformable ring are further adapted to wedge against the inner surface of the acetabulum without damaging the inner surface of the acetabulum.

10. The ancillary tool of claim 1, wherein the elastically deformable ring comprises an outer shape that is substantially complementary to the inner surface of the acetabulum.

11. The ancillary tool of claim 1, wherein an outer surface of the elastically deformable ring is configured to not damage the inner wall of the acetabulum when the outer surface participates in wedging of the inner wall of the acetabulum.

12. An ancillary tool for positioning and seating a prosthetic acetabulum in an anatomical or prosthetic cavity of a patient's hip, the tool comprising a handle that includes a rod having a threaded medial portion and a threaded distal portion, a movable sleeve non-rotatably coupled to the rod to move in distal and proximal directions on the rod, a grip adapted to rotate on the threaded medial portion of the rod to move the sleeve, a movable head adapted to move in distal and proximal direction on the rod and engages an endpiece, the endpiece having an elastically deformable ring including a plurality of petals mounted on a rigid part that contains a threaded portion to secure the endpiece to the rod, wherein the petals have outer surfaces adapted to engage the inner surface of a prosthetic acetabulum when the head is forced on inner surfaces of the petals.

13. The ancillary tool of claim 12, wherein the grip is adapted to longitudinally move the sleeve and the movable head into contact with the endpiece to radially expand the petals from a first configuration to a second configuration and secure the endpiece in the prosthetic acetabulum by gripping the inner surface of the prosthetic acetabulum with the outer surfaces of the petals.

14. The ancillary tool of claim 12, wherein the petals are connected to the rigid part of the endpiece by elastically deformable connecting zones.

15. The ancillary tool of claim 12, wherein the petals are adapted to move apart radially in a homogenous manner when contacted by the head.

16. The ancillary tool of claim 12, wherein the petals move radially in order to contact the inner surface of the acetabulum.

17. The ancillary tool of claim 12, wherein the tool includes a knob fixed to a proximal end of the tool.

18. The ancillary tool of claim 17, wherein the tool is adapted to transmit an impact force imparted on the knob to the proximal end of the tool.

19. The ancillary tool of claim 9, wherein the elastically deformable ring is elastic such that the ring expands from a first configuration to a second configuration when the head engages the ring and contracts substantially to the first configuration when the first force is removed.

20. An ancillary tool kit for positioning and seating a prosthetic acetabulum in an anatomical or prosthetic cavity of a patient's hip, the kit comprising:
a plurality of endpieces, each endpiece having an elastically deformable ring including a plurality of petals mounted on a rigid part, the rigid part containing a threaded portion and a stop surface; and
a tool comprising a handle that includes a rod having a threaded medial portion and a threaded distal portion, a movable sleeve adapted to move in distal and proximal directions on the rod, a grip adapted to rotate on the threaded medial portion of the rod to move the sleeve, a movable head adapted to move in distal and proximal direction on the rod and to engage one of the plurality of endpieces, the threaded portion of the rigid part of the endpieces adapted to secure the endpieces to the threaded distal portion of the rod, the stop surface of the rigid part of the endpieces adapted to abut the moveable head when the moveable head is fully advanced relative to one of the endpieces, wherein the petals have outer surfaces adapted to engage the inner surface of a prosthetic acetabulum when the head is forced on inner surfaces of the petals.

21. The ancillary tool kit of claim 20, wherein the plurality of endpieces includes endpieces that vary in size in order to accommodate a variety of different sized prosthetic acetabulum.

22. An Ancillary tool for implanting a prosthetic acetabular cup into an anatomical cavity or hip prosthesis of a patient, comprising a handle for manipulating the acetabular cup, which in its distal part is provided with a head for gripping the acetabular cup and in its proximal part is provided with a surface for applying an impaction force, and at least one cap is applied, which is adapted to be interlocked in a removable way with the distal end of the handle, defining at the same time a face for wedging the acetabular cup and an opposite face for the cap to interact with the head of the handle, wherein the cap has a base and a crown, which crown is connected elastically to the base so that it may be distorted radially in relation to the longitudinal axis of the cap and comprises several lobes, the faces for wedging and interacting being made up respectively of the external surfaces and internal surfaces of each of these lobes; wherein the tool has a first configuration in which the head is interlocked with the distal end of the handle and the crown is radially contracted toward the longitudinal axis of the cap and a second configuration in which the head is interlocked with the distal end of the handle and is disposed in the crown and radially distorts the crown away from the longitudinal axis.

23. The ancillary according to claim 22, wherein the crown is connected elastically to the base so that it may be distorted radially over more or less the whole periphery of the crown.

24. The ancillary according to claim 22, wherein the cap comprises at the same time a first part, including the base and the crown, and a second part, which is more rigid than the first part, interlocking with the first part and provided with means of interlocking in a removable way at the distal end of the handle.

25. The ancillary according to claim 24, wherein the second part of the cap is made up of a metal insert, which is fixed to the first part.

26. The ancillary according to claim 24, wherein the second part of the cap delimits a stopping surface for the head of the handle in the longitudinal direction of the handle.

27. The ancillary according to claim 24, wherein the first part of the cap has at least one surface for transmitting the impaction force between the handle and the acetabular cup.

28. The ancillary according to claim 22, wherein the head of the handle defines an inclined surface, which is adapted to cooperate with the face for interacting with the cap.

29. The ancillary according to claim 22, wherein the handle comprises a rigid rod, on which the head is fitted in a moveable way, as well as means of entrainment of the head in relation to the rod in a translatory movement in the longitudinal direction of the rod.

30. The ancillary according to claim 29, wherein the handle comprises a sleeve, which is arranged coaxially to the rod, at the distal end of which the head is fixed rigidly, and in that the means of entrainment of the head in relation to the rod comprise a handgrip, which is screwed onto the rod and connected in translation with the sleeve, this sleeve being immobilised in rotation in relation to the rod.

31. The ancillary according to claim 30, wherein a ring is interposed axially between the sleeve and the handgrip, which is screwed on.

\* \* \* \* \*